United States Patent [19]

Taft

[11] 4,002,171

[45] Jan. 11, 1977

[54] WATER-DISPERSIBLE IONIC POLYURETHANE BINDER FOR NONWOVEN FABRICS

[75] Inventor: Arnold Jay Taft, East Brunswick, N.J.

[73] Assignee: Personal Products Company, Milltown, N.J.

[22] Filed: Mar. 17, 1975

[21] Appl. No.: 558,989

[52] U.S. Cl. .............................. 128/284; 128/287; 128/290 R; 260/77.5 Q; 428/284; 428/286; 428/425; 428/290; 428/303

[51] Int. Cl.² .................. A61F 13/16; C07C 87/30

[58] Field of Search ... 260/78.3, 29.2 TN, 77.5 TB, 260/77.5 Q, 77.5 AN; 428/290 R, 423; 128/284, 287, 290

[56] References Cited

UNITED STATES PATENTS

| | | | |
|---|---|---|---|
| 3,479,310 | 11/1969 | Dietrich et al. | 260/77.5 AM |
| 3,527,221 | 9/1970 | Croon et al. | 128/287 |
| 3,640,967 | 2/1972 | Konig et al. | 260/77.5 D |
| 3,714,095 | 1/1973 | Reischl et al. | 260/29.2 TN |
| 3,753,826 | 8/1973 | Plummer | 428/290 |
| 3,778,476 | 12/1973 | Rembaum et al. | 260/77.5 Q |
| 3,804,092 | 4/1974 | Tune | 128/284 |

Primary Examiner—George F. Lesmes
Assistant Examiner—R. J. Roche
Attorney, Agent, or Firm—Jason Lipow

[57] ABSTRACT

A binder for nonwoven fabrics is provided comprising a cationic polyurethane having an ionic charge density sufficient to render the fabric dispersible in aqueous solutions of relatively low ionic strength yet resistant to body fluids. The water-dispersible nonwoven fabrics comprise one or more layers of substantially uniformly laid fibers bound with the cationic polyurethane; exhibit good tensile strength in the presence of body fluids such as urine, blood and menstrual fluid; and can be incorporated in body fluid-retaining products such as sanitary napkins, disposable diapers, surgical dressings and the like. Binders containing condensation residues of a polyisocyanate with an aliphatic polyester polyol are biodegradable.

21 Claims, 5 Drawing Figures

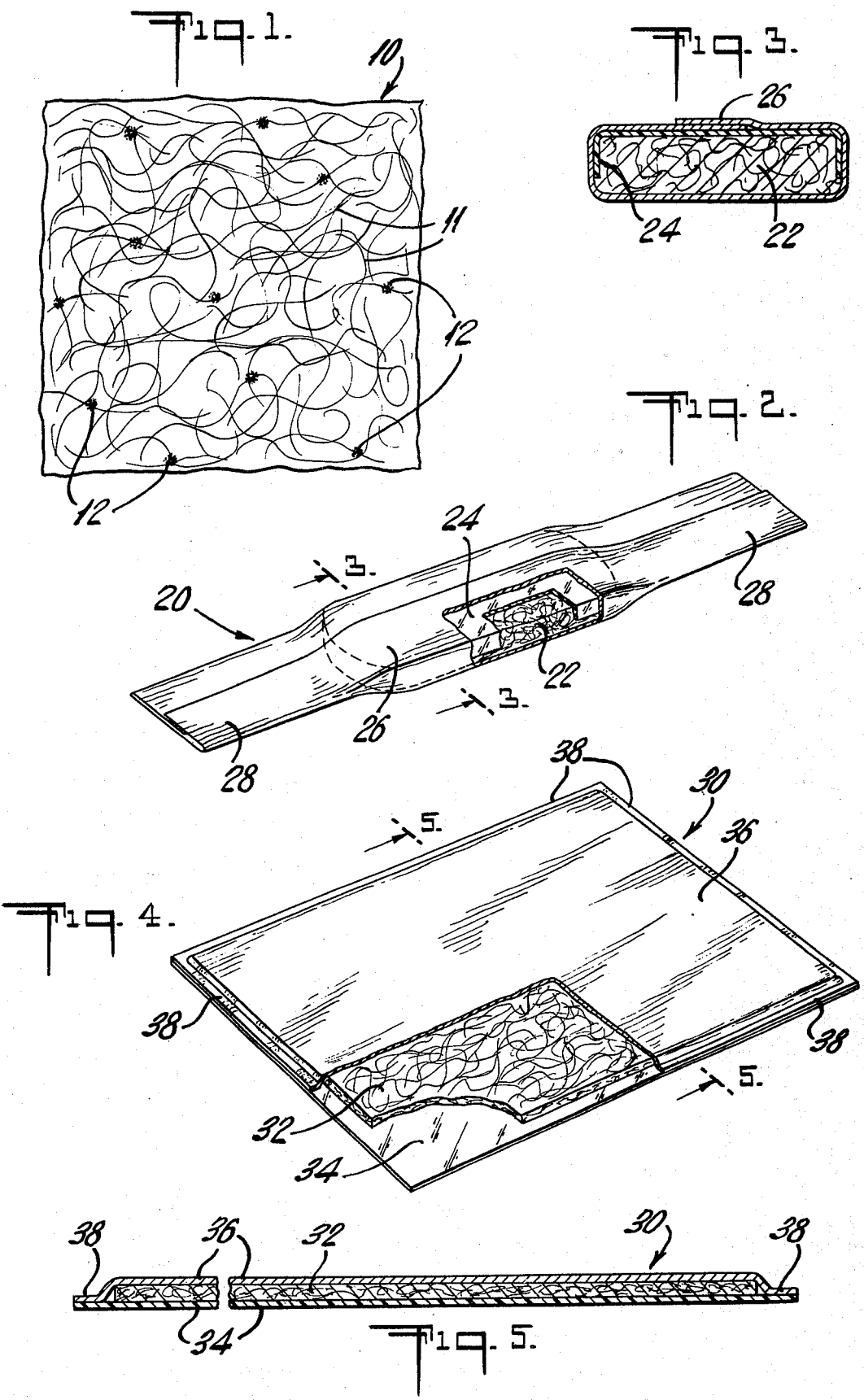

WATER-DISPERSIBLE IONIC POLYURETHANE BINDER FOR NONWOVEN FABRICS

BACKGROUND OF THE INVENTION

This invention concerns water-dispersible binders and the incorporation of such binders in products used to retain fluids exuded from the body such as blood, menstrual fluid and urine. Specifically, the binders and nonwoven fabrics of this invention are useful in connection with absorbent products such as sanitary napkins, diapers, dressings and the like. The fabrics of this invention exhibit adequate tensile strength and retain their structural integrity when in contact with the aforesaid body fluids, yet are readily dispersible in water or aqueous solutions of relatively low ionic strength so that the absorbent product may be flushed away after use.

Nonwoven fabrics are widely used as components of such disposable goods as sanitary napkins, diapers, bandages, and the like. Such fabrics, if they are to function effectively, must maintain their structural integrity, as well as exhibit satisfactory tensile strength, when they are wet or damp with the various body fluids, for example, blood, menstrual fluid and urine, with which they come into contact during use. It has been recognized that if such nonwoven fabrics, while retaining their strength in body fluids, were to lose substantially all their tensile strength when exposed to water and become readily dispersible therein, disposal problems would be substantially eliminated since the fabrics could be easily and conveniently flushed away in a water closet.

Unfortunately, in an attempt to provide nonwoven fabrics having certain desirable in-use characteristics, prior methods have rendered the fabric nondispersible in water. For example, nonwovens have been bonded with body fluid-insoluble resins which impart in-use strength. Generally, however, such resins have been water-insoluble as well and have impeded disposal of the fabric by flushing. Therefore, less desirable methods of disposal such as incineration or dumping must be employed.

Heretofore, the choice of suitable binders of water-dispersible products has been extremely limited in that the properties of binders to impart to fabrics both the characteristics of satisfactory in-use strength and water-dispersibility are infrequently found in combination. For example, the binder must impart sufficient strength for the fabric to resist disintegration for a reasonable period of time when the nonwoven fabric is in use, i.e., the binder just be insoluble or at least only slightly soluble in body fluids and must exhibit substantial tensile strength when subjected to such fluids. In addition, a suitable binder must provide the fabric with sufficient abrasive strength to withstand wear and tear when the product is one which is to be worn, such as a dressing, a sanitary napkin or a diaper. In apparent conflict with these properties, the binder must allow the fabric to be readily dispersed in water so that the absorbent product can be conveniently flushed away after use and also insure that the fabric is soft and flexible so as to be comfortable to the user. These criteria are difficult to meet with a single material, and hence, a choice of binders, suitably possessing both properties, has heretofore been extremely limited.

SUMMARY OF THE INVENTION

The present invention contemplates a binder for fibers in nonwoven fabrics used in products for retaining body fluids, which binder is dispersible in water and resistant to body fluids. The binder comprises a resin of cationic polyurethane having a repeating unit of the formula:

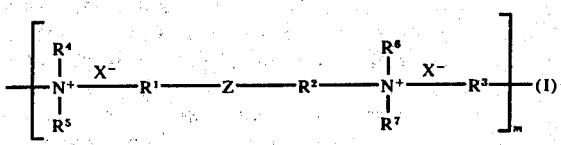

wherein $R^1$ and $R^2$ are selected from the group consisting of $-CH_2-$ and alkylene containing 2 to 4 carbon atoms, inclusive; Z is a linking condensation residue of a polyisocyanate with a polyol and contains at least four urethane linkages, $R^3$ is alkylene containing 2 to 4 carbon atoms, inclusive; $R^4$, $R^5$, $R^6$ and $R^7$ are lower alkyl groups containing 1 to 4 carbon atoms, inclusive; X is a halogen selected from the group consisting of chlorine and bromine; and m is an integer of sufficient magnitude to provide a polymer having a sufficient molecular weight to form a solid material. The equivalent weight of the polymer (based on ionic nitrogen) is no greater than about 2000. Preferably, m has a value of about 10 to about 50.

It has now been discovered that these binders exhibit the unusual properties of retaining their tensile strength in salt solutions such as body fluids while readily dispersing in tap water.

The bonded nonwoven fabric of this invention, in addition to having good strength when dry, and satisfactory strength and abrasion resistance in the presence of most body fluids, such as urine, blood, menstrual fluid and the like, is easily dispersible in water and hence, is flushable in home water closets and standard sewer or septic systems. In this connection, when an article is referred to herein as being flushable, it is meant that that article can be deposited in, and flushed through a water closet without any undue clogging of the water closet or its auxiliary piping. When such an article is referred to herein as being water-dispersible, it is meant that that article loses its integrity when placed in water.

The improved nonwoven fabric of this invention comprises one or more layers of substantially uniformly laid fibrous webs and the herein prescribed binder in an amount of about 4% to about 35% by weight of the web.

The fabrics prepared in accordance with this invention have good dry tensile strength depending upon, among other things, the amount of binder applied to the fabric and the manner in which it is applied. They are abrasion resistant and retain a significant part of their dry tensile strength in solutions containing about 0.8% or more by weight of sodium chloride, and yet are readily dispersible in water.

In another aspect of this invention, the nonwoven fabrics are incorporated into such body fluids absorbent products as sanitary napkins, diapers, surgical dressings and the like. These products generally include an absorbent core, comprising one or more layers of an absorbent fibrous material. The core may also comprise one or more layers of a fluid-pervious element, such as fibrous tissue, gauze, plastic netting, etc. These are generally useful as wrapping materials to hold the components of the core together. Additionally, the core may comprise a fluid-impervious element or barrier means to preclude the passage of fluid through the core and on the outer surfaces of the product. Preferably, the barrier means also is water-dispersible. A film of a cationic polyurethane having substantially the same composition as the aforesaid water-dispersible binder is particularly well-suited for this purpose. In accordance with this aspect of the instant invention, a body fluid retaining product is provided having a nonwoven fabric overlying an absorbent core, the nonwoven fabric comprising a web of overlapping fibers and the water-dispersible binder in an amount of about 4 to about 35% by weight of the web.

BRIEF DESCRIPTION OF THE DRAWINGS

FIG. 1 is a plan view of a bonded nonwoven fabric in accordance with the present invention;

FIG. 2 is a perspective view of a sanitary napkin embodying this invention with parts broken away to show the interior construction thereof;

FIG. 3 is a cross-sectional view taken along plane 3—3 of FIG. 2;

FIG. 4 is a perspective view of a disposable diaper embodying this invention with parts broken away to show the interior construction thereof; and FIG. 5 is a cross-sectional view taken along plane 5—5 of FIG. 4.

DETAILED DESCRIPTION OF THE INVENTION

The cationic polyurethane binders of this invention change their molecular configuration in response to a change in the ionic strength of the medium to which these binders are exposed. In a medium of relatively low ionic strenth such as water, the ion-bearing polyurethane molecules generally assume a flexible linear, helical rod, or elliptical configuration, but the molecules change to a randomly convoluted configuration as the ionic strength of the medium increases. Binders prepared in accordance with this invention from ionic polyurethanes have maintained their structural integrity when immersed in aqueous 1 wt-% sodium chloride solutions, yet the same binders have been found to readily disintegrate or become solubilized in tap water or distilled water. The binder resins can be prepared by condensing a polyisocyanate with a polyol and with a tertiary amino alcohol to produce a tertiary amine-capped condensation prepolymer which is then further reacted with a dihaloalkene to produce the polymeric material having the repeating unit shown in Formula I hereinabove. Preferably, the molecular weight of the cationic polymeric binders is about 8,000 to about 50,000.

The reaction between the polyisocyanate and the polyol is the well-known urethane forming reaction which is preferably conducted in a solvent under anhydrous conditions and in the presence of a suitable catalyst such as stannous octoate, dibutyl tin dilaurate, or the like.

Polyisocyanates suitable for the purposes of the present invention can be aliphatic, aromatic, mixed aliphaticaromatic, and can be of monomeric or polymeric length. Typical of such polyisocyanates are tolylene-2,4-diisocyanate (TDI); diphenylmethane-4,4′-diisocyanate (MDI); tolylene-2,3-diisocyanate; hexane-1,6-diisocyanate; naphthelene-1,5-diisocyanate; diphenyl-3,3′-dimethyl-4,4′-diisocyanate; diphenyl-3,3′,-dimethoxy-4,4′-diisocyanate dictyl ether; 3-(diethlyamino)-pentane-1,5-diisocyanate; butane-1,4-diisocyanate; cyclohex-4-ene-1,2-diisocyanate; benzene-1,3,4-triisocyanate; naphthalene-1,3,5,7-tetraisocyanate; naphthalene-1,3,7-triisocyanate; toluidine diisocyanate; isocyanate-terminated prepolymers; polyarylpolyisocyanates; and the like. Illustrative of the commercially available polyarylpolyisocyantes is a polymethylene polyphenyl polyisocyanate known under the designation PAPI-1 and available from the Upjohn Company. This particular polyisocyanate has an average molecular weight of about 380 and an average of about 3 isocyanate groups per molecule. Another suitable polyisocyanate is a poly (1,4-oxybutylene)-based diisocyanate terminated prepolymer known under the designation ADIPRENE L-100 (molecular weight about 2050) and ADEPRENE L-167 (molecular weight about 1330), both available from E. I. duPont de Nemours & Company of Delaware. Still another commercially available higher molecular weight polyisocyanate is a polyester terminated with isocyanate groups known under the designation MULTRATHANE-242 F available from the Mobay Chemical Corporation of Pittsburgh, Pa. Also suitable is a triisocyanate derivative of glycerol and ricinoleic acid known under the designation SOLITHANE 113 available from the Thiokol Chemical Corporation of Delaware.

Suitable polyols for the present purposes are the polyether polyols such as polyethylene glycol, polypropylene glycol, polybutylene glycol and the like, which have ether linkages, or the polyester polyols such as polycaprolactone, and the like which have ester linkages and polyester-polyether block copolymers thereof which have both ether linkages and ester linkages. For producing a biodegradable cationic polyurethane, particularly preferred are the aliphatic polyester polyols such as polycaprolactone having a molecular weight in the range of about 800 to about 2000, alone or in combination with a polyether polyol. Preferably, the mole ratio of polyester-to-polyether polyols is about 1 to about 3.

Illustrative of the tertiary amino alcohols are 1,3-bis(dimethylamino)-2-propanol; 2-dimethylaminoethanol; p-dimethylaminophenol; and the like.

In preparing the tertiary amine-capped prepolymers, the foregoing reactants can be added sequentially or in a single step, as desired. Suitable solvents for carrying out the reaction are methylethylketone, dimethylformamide, tetrahydrofuran, dimethylsulfoxide (DMSO), and the like.

Thereafter, the prepared tertiary-amine prepolymer is alkylated, i.e., quaternized, by adding a dihaloalkene such as trans-1,4-dichloro-2-butene (TDCB), trans-1,4-dibromo-2-butene 3,4 dichloro-1-butene or the like, to the reaction mixture at a temperature of about 20° C. to about 100° C., and preferably at a temperature of about 50° C. to about 60° C. An unsaturated alkylating agent should be used in order to enhance the quaternization reaction. The resulting ionic polyurethane polymer can then be used as a binder for nonwoven fibrous webs, or can be cast into films of desired thickness which are suitable for use as barrier films as more fully set forth in my copending application, Application Ser. No. 559,205, filed Mar. 17, 1975 and incorporated herein, by reference.

The overall reaction sequence can be illustrated as follows:

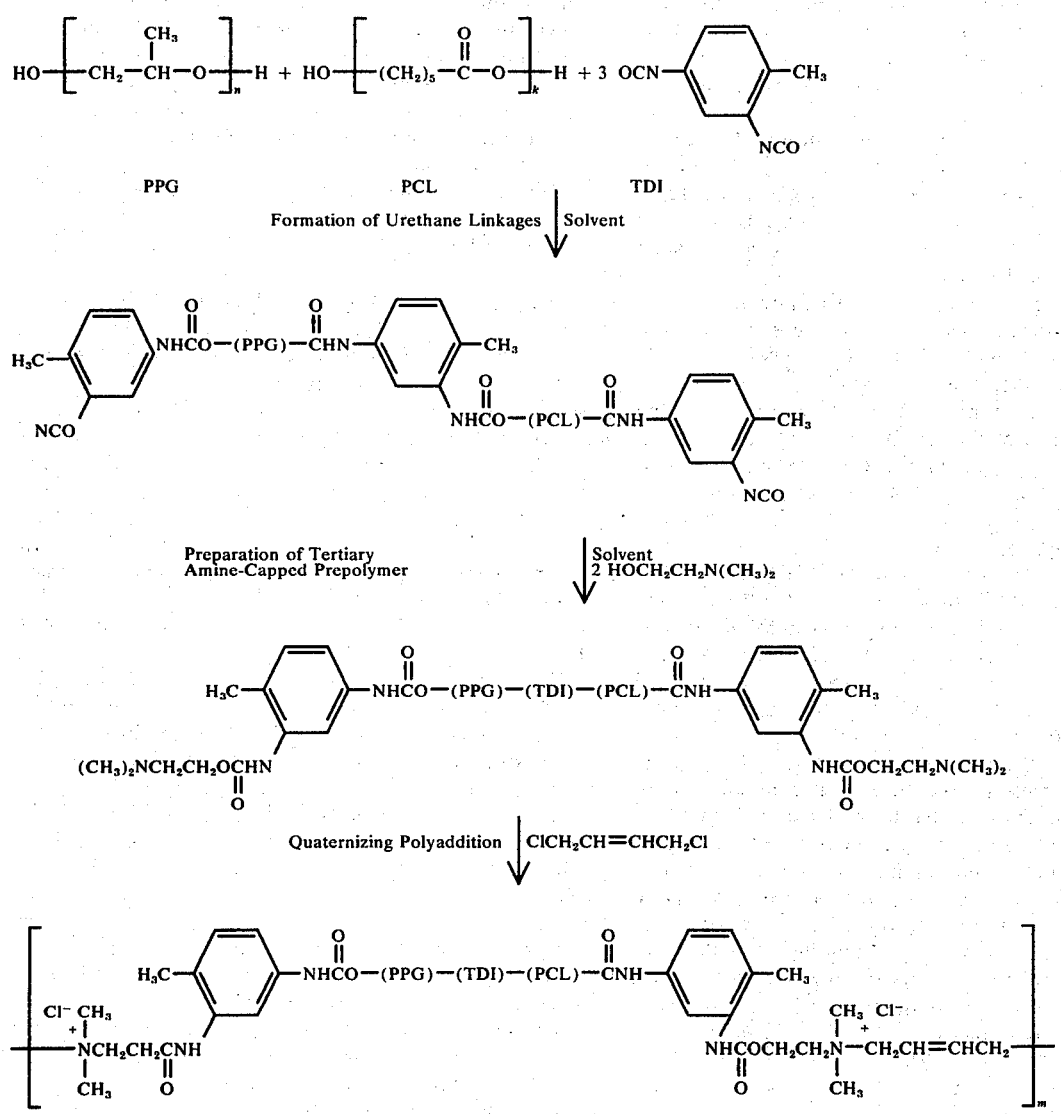

The binders of this invention, derived from ionic polyurethane resins, are uniquely suited for use in flushable products used in contact with such body fluids as blood, menstrual fluid, urine, etc. These fluids, in general, exhibit properties which, with respect to the binders are analogous to an aqueous salt solution having a salt content which varies from about 0.8 to about 1.5 percent by weight of sodium chloride. On the other hand, tap water normally supplied to water closets and the like generally has an extremely low salt concentration of less than about 250 parts per million of chloride ion. It has been discovered that the binders, and thus the fabrics, of this invention maintain their integrity for a substantial period of time in solutions having a salt concentration exhibiting the properties of body fluids, whereas, surprisingly, these binders display a far lower resistance to dispersion in tap water. In addition, by modifying the ionic charge density of these binders, the salt resistance and water dispersibility of the binders can be modified to suit the particular purposes of this invention, i.e., binders which will adequately provide a resistance to body fluids for a suitable length of time yet which will disperse in tap water can be prepared.

Specifically, by lowering the ionic charge density, the binders of this invention become more resistant to dispersion in water. However, if the ionic charge density is increased, the binders maintain structural integrity in body fluids yet remain water dispersible. On the other hand, if the ionic charge density is too high, the binders, and hence the fabrics, lose structural integrity in body fluids. The ionic charge density for the ionic polyurethane polymer is an inverse function of the equivalent weight of the polymer expressed as the ratio of the molecular weight of the repeating unit in the polymer chain divided by the number of $N^+$ in the repeating unit, i.e., as the equivalent weight increases, the ionic charge density decreases and vice versa. In general, an equivalent weight of about 500 to about 2000 is desirable for the present binders. Preferably, the equivalent weight should be in the range of about 750 to about 1400. While the resistance of the binders to salt solutions having a salt concentration exhibiting the properties of body fluids increases with decreasing charge density, the ability to disperse readily in tap water is maintained until relatively low charge density values are reached. Adequate tap water dispersibility is achieved, however, when the equivalent weight is maintained at a value not greater than about 2000.

The binders of this invention are highly compatible with a great variety of plasticizers; thus such plasticizers may be incorporated therein to improve such binder characteristics as flexibility and resistance to abrasion. These properties are particularly important when the binders are used in connection with items to be worn such as the aforementioned sanitary napkins, diapers and the like. For these purposes, water soluble plasticizers such as glycerol and polyethylene glycol can be used, as well as water-insoluble plasticizers such as castor oil, and the like.

The foregoing cationic polyurethane resins either plasticized or not are used to bond a web of fibers to provide the nonwoven fabric of this invention. Suitable webs comprise most of the well-known fibers, the choice depending upon, for example, fiber cost and the intended end use of the finished fabric. For instance, the web or base layer may include natural fibers such as cotton, linen, jute, hemp, cotton linters, wool, wood pulp, etc.

Similarly, regenerated cellulosic fibers such as viscose rayon and cuprammonium rayon, modified cellulosic fibers, such as cellulose acetate, or synthetic fibers such as those derived from polyvinyl alcohol, polyesters, polyamides, polyacrylics, etc., alone or in combination with one another, may likewise be used. Natural fibers may be blended with regenerated, modified, and/or synthetic fibers if so desired.

The length of the fiber is important in producing the fabrics of the present invention. The minimum length of the fibers depends on the method selected for forming the base layer. For example, where the base layer is formed by carding, the length of the fiber should usually be a minimum of one-half inch in order to insure uniformity. Where the base layer is formed by air deposition or water deposition techniques, the minimum fiber length may be about 0.05 inch. It has been found that when a substantial quantity of fibers having a length greater than about 2 inches is placed in the fabric, though the fibers will disperse and separate in water, their length tends to form "ropes" of fibers which are undesirable when flushing in home water closets. It is preferred that the fiber length be 1½ inches or less so that the fibers will not rope when they are flushed through a toilet.

The base layers suitable for conversion into the fabric of the present invention may be formed by carding, garnetting, air deposition, water deposition, or any of the other various techniques known in the art. The fibers in the layer may be oriented predominantly in one direction as in a card web or a card web laminate or they may be randomly oriented as in a layer formed by air deposition techniques. For sanitary napkin coverings, disposable diaper facings and similar uses where the fabric is to be flushable, the web is fairly thin and should weigh between 150 to 400 grains per square yard. Where the fabric must possess a substantial amount of strength, uniform fiber distribution is important so as to avoid weak spots in the final nonwoven fabric. Uniform base layers may be produced by carding in which case it is advantageous to use fibers which have good carding characteristics and can be blended into a uniform carded web with facility. Fibers of viscose rayon and cotton are both satisfactory in this respect.

The amount of cationic polyurethane binder distributed in the base layer should be from about 4 to 35 percent by weight of the final nonwoven fabric. If less than about 4 percent of the binder is employed, the fabric usually does not have sufficient strength and abrasion resistance. If more than about 35 percent of the binder is employed, the fabric may lose desirable properties such as absorbency and softness.

It is preferred that the amount of binder present be in the range of about 5 to about 20 percent by weight of the final nonwoven web in order to ensure optimum water dispersibility.

The binder may be distributed in the base layer by printing, spraying, impregnating or by any other technique whereby the amount of binder may be metered and distributed uniformly within the base layer. The binder may be distributed throughout the entire base layer or it may be distributed therein in a multiplicity of small closely spaced areas. The binder may also be distributed in lines running across, or at an angle to, the width of the web or in separate small shaped areas having circular, angular, square, or triangular configurations. It is preferred that when the binder is applied to the fibrous web there be left unbonded areas in the layer. These unbonded areas of fibers readily absorb water which ultimately finds its way to the binder areas and makes the fabric dispersible in shorter periods of time.

For ease of application to the base fibrous layer, the binder may be dissolved in water, or in non-aqueous solvent such as methanol, ethanol, or the like, to provide solutions containing up to about 30 percent by weight of binder solids. Plasticizers, such as glycerol, polyethylene glycol, castor oil, and the like, may be added to the solution of the binder resin, the amount of such plasticizers varying according to the softness required in the final fabric. Perfumes, coloring agents, antifoams, bactericides, surface active agents, thickening agents, fillers and similar additives can also be incorporated into the solution of binder if so desired. Other water soluble or water dispersible binding agents such as polyvinyl alcohol or aqueous dispersions of, for example, polyvinyl chloride, polyvinyl acetate, polyacrylates, polymethacrylates, copolymers of acrylates and methacrylates, copolymers of vinyl acetate with acrylates and/or methacrylates and copolymers of acrylates and/or methacrylates with vinyl chloride can also be added to the ionic polyurethane binder solution in order to obtain bonded fabrics having various desired properties.

Referring now to the drawings and specifically to FIG. 1, a water dispersible nonwoven fabric 10 comprises a web of overlapping, substantially uniformly laid fibers 11 having substantially uniformly distributed therein a cationic polyurethane binder 12.

FIGS. 2 and 3 of the drawing illustrate an embodiment of the water dispersible nonwoven fabric of this invention as used with sanitary napkin 20.

Napkin 20 comprises an absorbent core which is enveloped by fluid-pervious cover 26 comprising the bonded nonwoven fabric of this invention. The absorbent core comprises pad 22 of absorbent fibrous material such as comminuted wood pulp fibers, cotton linters, rayon fibers, cotton staple, bleached sulfite linters, other cellulosic or modified cellulosic fibers and the like. The absorbent core is covered on one side by fluid impervious element or barrier means 24 which, for example, may be a thin polyethylene sheet, a cationic polyurethane film, or any other suitable material. As best seen in FIG. 3, barrier means 24 overlies the sides and the bottom surface (the surface normally worn away from the body) of absorbent pad 22. The lateral edges of cover 26 are overlapped and secured on the bottom surface of napkin 20. Cover 26 is also extended beyond the ends of the absorbent core to form attachment tabs 28. While FIGS. 2 and 3 illustrate a tabbed sanitary napkin, it will be understood by one skilled in the art that the advantages accruing to the use of the nonwoven fabrics of this invention are equally applicable to a tabless product, e.g., one where tabs are not used as attachment means, and instead other attachment means such as, for example, adhesive means, are employed. The absorbent core can also comprise, in addition to the absorbent pad and barrier means, a fluid pervious element such as gauze, tissue, plastic netting and the like if increased strength and/or dimensional stability are desired. Also, the fluid pervious cover of this invention need not completely surround the absorbent pad as illustrated in FIGS. 2 and 3. For example, a fluid pervious cover could be provided so that the edges thereof are adhered to the edges of the barrier means; in such a case, the barrier means and fluid pervious cover would cooperate to form an enclosure for the pad of absorbent fibrous material.

The nonwoven fabric of this invention is uniquely suited to serve as a fluid pervious covering in a sanitary napkin, such as shown in FIGS. 2 and 3, because it is resistant to abrasion and exhibits satisfactory tensile strength when it has been dampened or wetted with menstrual fluid, which has a salt content of about 0.8 to about 1.5 percent by weight. The fabrics of this invention are resistant to solutions containing more than about 0.8% salt, and notwithstanding such salt resistance, the fabrics are completely dispersible when introduced into water or into salt solutions whose salt content is less than about 0.8% by weight. The use of a water dispersible material for the barrier means and the water dispersible absorbent pad makes it possible for the sanitary napkin of FIGS. 2 and 3 to be conveniently and completely disposed of by flushing through a water closet.

Alternatively, the illustrated napkin may be provided with a non-water dispersible barrier means and a water-dispersible absorbent pad. In that case, fluid pervious covering 26 is first removed or at least torn away so that the barrier means can be separated from the pad; thereafter the pad and covering can be dropped into a water closet for disposal. In either case, the unique nonwoven fabric of this invention will be completely dispersed in a water closet under the swirling action of the water supplied thereto, and will not impair the normal operation of the water closet and associated plumbing.

FIGS. 4 and 5 of the drawing illustrate another embodiment of the water dispersible nonwoven fabric of this invention as used with disposable diaper 30.

Diaper 30 comprises an absorbent core and a fluid-pervious facing 36 comprising the nonwoven fabric of this invention. The absorbent core comprises an absorbent layer 32 of fibrous material such as comminuted wood pulp fibers, cotton linters, rayon fibers, cotton staple, bleached sulfite linters, other cellulosic or modified cellulosic fibers, and the like. On the other side of the absorbent core is provided a body fluid impervious element or barrier means 34 which overlies the bottom surface of absorbent layer 32. Barrier means 34 may comprise, for example, a thin sheet of polyethylene or other suitable material. Where barrier means 34 is not water-dispersible, it is preferred that it can be easily removable from the remainder of the diaper so as to minimize disposal problems. Fluid pervious facing 36 overlies the inner or top surface of absorbent layer 32. In the embodiment illustrated in FIGS. 4 and 5, it will be observed that barrier means 34 and fluid pervious facing 36 are substantially coextensive and are joined together at their peripheries 38 by methods well-known in the art such as adhesive bonding, stitching, or heat sealing techniques.

While FIG. 4 illustrates a disposable diaper having a particular construction, it will be recognized by those skilled in the art that the advantages accruing to the use of the nonwoven fabrics of this invention are equally applicable to disposable diapers having other, widely varying constructions. The absorbent core is not limited to the structure illustrated, but may include a fluid pervious element, such as gauze, tissue, plastic netting and the like, if it is desired to increase strength and/or structural integrity.

The nonwoven fabric of this invention is uniquely suited to serve as fluid-pervious facing 36 of disposable diaper 30 as shown in FIG. 4 because it is resistant to abrasion and exhibits acceptable tensile strength when dampened or wetted with urine. Urine has a salt content of about 0.8% to about 1.5% by weight and, as already indicated, the nonwoven fabrics herein are resistant to solutions containing about 0.8% or more by weight of sodium chloride. It will be apparent that by employing a waterdispersible, absorbent layer such as layer 32, diaper 30 can be safely and conveniently disposed of by flushing through a water closet. When diaper 30 has been provided with a barrier sheet that is not water dispersible, but has a water-dispersible, absorbent layer, then the layer and the facing may be safely flushed after they have been separated from the barrier means.

Those skilled in the art will readily understand that the water dispersible nonwoven web of this invention may be advantageously employed in the preparation of a wide variety of absorbent products designed to be contacted with body fluids. Many such absorbent products need only comprise a core of absorbent material in combination with said nonwoven fabric. For example, an absorbent surgical dressing could be made comprising a relatively thin, rectangular layer of absorbent material with the nonwoven fabric overlying one or more sides thereof. Similarly, as in the case of a tampon, the nonwoven fabric could overlie a cylindrical core of absorbent material. Alternatively, the core of absorbent material could be in the form of a sphere, a cube, a disc, or other desirable geometrical configuration.

The invention will be more readily understood by consideration of the following examples which describe specific embodiments exemplifying the invention and the methods of making and using the same.

EXAMPLE 1

A series of ionic polyurethane polymers are prepared using as the starting material a prepolymer obtained from the duPont Company and sold by them under the trademark ADIPRENE. This prepolymer consists of a diisocyanate terminated poly(1,4-oxybutylene) and has a number average molecular weight of about 1330. The prepolymer is combined with 2-dimethylaminoethanol in a benzene solution and allowed to react therewith at a temperature of 60°–70° C for about 1.5 hours. A quantity of trans-1,4,-dichloro-2-butene is then added to the reaction mixture which is then allowed to further react at the above given temperature for seven additional minutes. A quantity of 4,4'-methylene-bis-(2-chloroaniline) is then added to the system and the reaction mixture is then cured for about 18 hours at a temperature of about 50°–60° C. with stirring. The proportions of the components used and the resulting polymer equivalent weight (the molecular weight of the repeating unit divided by the number of $N^+$ in the repeating unit) are given in Table I below.

ture to about 50°–60° C. and adding a quantity of trans 1,4,-dichloro-2-butene.

The reaction mixture is cured by maintaining the mixture at about 50° to 60° C while stirring. The proportions of the various components, the curing times and the equivalent weight of the resulting ionic polyurethane polymers are given in Table II.

TABLE II

| Sample | Mole Ratio of Components | | | | | Curing Time (hrs) | Equivalent Weight |
|---|---|---|---|---|---|---|---|
| | Polycaprolactone Polyol | Polypropylene Glycol | Dimethylamino Ethanol | Tolylene Diisocyanate | Dichloro Butene | | |
| 3 | 0.25 | 0.75 | 4.0 | 3.0 | 2.1 | 18 | 780 |
| 4 | 0.25 | 0.75 | 2.0 | 2.1 | 1.0 | 18 | 1330 |
| 5 | 0.25 | 0.75 | 2.0 | 2.6 | 1.0 | 18 | 1380 |
| 6 | 0.25 | 0.75 | 2.0 | 2.6 | 1.2 | 18 | 1392 |
| 7 | 0.25 | 0.75 | 2.0 | 2.0 | 1.0 | 18 | 1320 |
| 8 | 0.25 | 0.75 | 4.0 | 3.0 | 2.1 | 18 | 780 |
| 9 | 0.25 | 0.75 | 2.0 | 2.1 | 1.0 | 18 | 1330 |
| 10 | 0.25 | 0.75 | 2.0 | 2.6 | 1.0 | 18 | 1380 |
| 11 | 0.25 | 0.75 | 4.0 | 3.0 | 2.0 | 24 | 790 |
| 12 | 0.25 | 0.75 | 4.0 | 3.0 | 2.0 | 144 | 790 |
| 13 | 0.25 | 0.75 | 2.0 | 2.6 | 1.2 | 24 | 1380 |
| 14 | 0.25 | 0.75 | 2.0 | 2.6 | 1.2 | 240 | 1380 |
| 15 | 0.25 | 0.75 | 2.0 | 2.2 | 1.0 | 24 | 1340 |
| 16 | 0.25 | 0.75 | 2.0 | 2.2 | 1.0 | 168 | 1340 |
| 17 | 0.25 | 0.75 | 2.0 | 2.2 | 1.0 | 24 | 1340 |
| 18 | 0.25 | 0.75 | 2.0 | 2.2 | 1.0 | 120 | 1340 |
| 19 | 0.25 | 0.75 | 4.0 | 3.0 | 2.0 | 24 | 790 |
| 20 | 0.25 | 0.75 | 4.0 | 3.0 | 2.0 | 216 | 790 |
| 22 | 0.25 | 0.75 | 2.0 | 2.1 | 1.0 | 24 | 1320 |
| 23 | 0.25 | 0.75 | 2.0 | 2.1 | 1.0 | 72 | 1320 |
| 24 | 0.25 | 0.75 | 2.0 | 2.1 | 1.0 | 24 | 1320 |
| 25 | 0.25 | 0.75 | 2.0 | 2.1 | 1.0 | 168 | 1320 |

Table I

| Sample | Molar Ratio of Components | | | | Equiv. Weight |
|---|---|---|---|---|---|
| | Prepolymer | 2-Dimethyl- amino Ethanol | Dichlor- obutene | Methylene Chloro- aniline | |
| 1 | 1 | 1.8 | 0.9 | 0.1 | 920 |
| 2 | 1 | 1.7 | 0.85 | 0.15 | 970 |

EXAMPLE 2

A second series of ionic polyurethanes, as prescribed herein, are prepared by combining, in methylethylketone, a quantity of polycaprolactone polyol having a number average molecular weight of about 2000 with polypropylene glycol having a number average molecular weight of about 2025 and 2-dimethylaminoethanol A quantity of 2,4 tolylene diisocyanate and stannous octoate (as catalyst) is added and the mixture is permitted to react at about 60° to 70° C for 6 hours. The resulting tertiary amine-capped prepolymer is then quaternized by lowering the reaction mixture tempera-

EXAMPLE 3

A third series of ionic polyurethanes, as prescribed herein, are prepared by combining a quantity of polypropylene glycol having a number average molecular weight of about 2025 with 2-dimethylaminoethanol. A quantity of 2,4-tolylene diisocyanate and stannous octoate (as catalyst) is added and the mixture is permitted to react at 60°–70° C for 6 hours. The resulting tertiary amine-capped prepolymers is then quaternized by adding a quantity of trans-1,4-dichloro-2-butene to the reaction mixture which is lowered to a temperature of about 50°–60° C and then cured for a specified period of time with mixing. The properties of the components, the curing times and the equivalent weight of the resulting ionic polyurethanes obtained are given in Table III.

TABLE III

| Sample | Mole Ratio of Components | | | | Cure Time (Hours) | Equivalent Weight |
|---|---|---|---|---|---|---|
| | Polypropylene Glycol | Dimethylamino Ethanol | Tolylene Diisocyanate | Dichloro Butene | | |
| 26 | 1 | 2.0 | 2.1 | 1.0 | 1 | 1340 |
| 27 | '' | '' | '' | '' | 7 | 1340 |
| 28 | 1 | 2.0 | 2.0 | 1.0 | 1 | 1320 |
| 29 | '' | '' | '' | '' | 24 | 1320 |
| 30 | '' | '' | '' | '' | 1 | 1320 |
| 31 | '' | '' | '' | '' | 24 | 1320 |

EXAMPLE 4

Films are prepared from the ionic polyurethanes of the foregoing examples to illustrate the dry strength properties of these films as well as the difference in wet properties when comparing their behavior in various liquid media.

In each case, the ionic polyurethane films are prepared by dissolving the ionic resin in methanol so as to form about 3–5% by weight methanol solutions. The above concentration gives good fluidity (a viscosity of about 15 cps at 25° C) and at these concentrations, films may be prepared having a thickness of from 0.5 to 3 mil while using reasonable volumes of solution. The films are cast in 8 × 8 inches Teflon-coated or silicone-coated pans. The data reported in Table IV below is based on film samples prepared as described above, each sample measuring 10 mm by 10 mm and being 2 mils thick. Reduced viscosity measurements as reported below are made by the method described in *Text Book of Polymer Science*, W. Billmayer, Interscience (1965). The solvent used in all cases for reduced viscosity measurements is dimethyl sulfoxide and for samples 3 through 10, the solution of polymer is at a concentration of 0.25% by weight, whereas for samples 11 through 31, the concentration is 2.0% by weight. Dry tensile and Ultimate Elongation data are obtained using an Instron Tensile Tester with the jaw space set at a distance of two inches and the crosshead speed maintained at 2 inches per minute.

The samples are tested to contrast the wet properties they exhibit in distilled water, in a 1% by weight sodium chloride solution and, for the two cases noted in Table IV, in pooled samples of menstrual fluid. The samples are immersed in each liquid media for the time specified below and the condition of the film at the end of this time period is noted either qualitatively or quantitatively. Qualitatively, the condition is alternatively described as Dissolved, Considerable Loss of Integrity (Consid. LOI, where the film has broken up into large fragments) or Complete Loss of Integrity (Comp. LOI, where the film has broken up into small fragments).

Where the wet properties are quantitatively expressed in Table IV, this data refers to the percent elongation or (EOL) in the original length of the film as a result of immersion; the greater the percent elongation, the weaker the film. It should be noted that where percent elongation is recordable, (i.e., where quantitative values are given), the film is stronger than those samples for which wet properties are reported qualitatively.

As Table IV clearly shows, all of the film samples cast had substantial dry strength properties. In accordance with the teachings of this invention, it should be noted that the wet properties varied greatly as the ionic strength of the liquid media increased. Specifically, in every case, the films were considerably weaker in solution distilled water solution as compared with a saline solution. As menstrual fluid is likewise comparable in ionic strength to the saline test solution, the data (see samples 3 and 5) shows that this differential wet property of the films carries through for menstrual fluid as well, making these resins particularly well suited for feminine hygiene products where it is desirable that the resin exhibit greater strength in menstrual fluid then in relatively non-ionic water media such as, for example, tap water. In this connection, it should be noted that several film samples were tested by immersion into tap water, in addition to the usual distilled water vs. 1% sodium chloride solution comparison, in order to evaluate the effect of the salt content in the municipal water supply. The results obtained with tap water were essentially comparable to those obtained with distilled water.

EXAMPLE 5

Nonwoven sanitary napkin covers are prepared from a fibrous web of rayon fibers treated with various ionic polyurethane binders of this invention, being identified below by sample number (see Table 1). In each case, the binder is distributed in the web as an aqueous solution or dispersion containing the quantity of resin indicated as % solids in Table V. The treated webs are then dried and the % add-on of resin, based on the untreated web, is measured and reported below.

Sanitary napkins are then prepared, using these webs as the cover material and having the construction of a commercially available flushable napkin sold by Personal Products Company, Milltown, N.J., a corporation of the state of New Jersey, as MODESS flushable feminine napkins. The construction of these napkins is generally similar to that illustrated in FIGS. 2 and 3. Fifteen napkins are prepared for each of the fabrics to be tested. The sanitary napkins so made are then tested for

TABLE IV

| | | | DRY PROPERTIES | | | WET PROPERTIES (EOL %) | | |
| | | | | | | | SOLUTION | |
| Sample | Cure Time (hrs.) | Equiv. Wt. | Reduced Viscosity (Centipoises) | Tensile Strength (PSI) | Ultimate Elongation (%) | Immersion Time (Min.) | Distill. $H_2O$ | 1% Saline $H_2O$ | Menstrual Fluid |
|---|---|---|---|---|---|---|---|---|---|
| 1 | 18 | 920 | — | — | — | 20 | Dissolved | 20 | — |
| 2 | 18 | 970 | — | — | — | 20 | 70% | 10 | — |
| 3 | 18 | 780 | 1.18 | 120 | 510 | 20 | Dissolved | 60 | 20 |
| 4 | 18 | 1330 | 0.35 | 60 | 210 | 20 | Comp. LOI | 10 | — |
| 5 | 18 | 1380 | 0.86 | 120 | 920 | 20 | Consid. LOI | 15 | 5 |
| 6 | 18 | 1390 | 0.77 | 100 | 1020 | 20 | Comp. LOI | 15 | — |
| 10 | 18 | 1380 | 0.37 | 60 | 480 | 20 | — | — | — |
| 11 | 24 | 790 | 0.46 | 120 | 420 | 1/60 | Cons/Dissol. | 15/50 | — |
| 12 | 144 | 790 | 0.55 | 160 | 880 | 1/60 | 70/Dissol. | 15/70 | — |
| 13 | 24 | 1380 | 0.37 | 100 | 540 | 1/60 | 50/Consid. | 5/10 | — |
| 14 | 240 | 1380 | 0.93 | 200 | 1200 | 1/60 | 60/Comp. | 5/20 | — |
| 15 | 24 | 1340 | 0.36 | 80 | 370 | 1/60 | 90/Comp. | 5/10 | — |
| 16 | 168 | 1340 | 0.44 | 140 | 280 | 1/60 | 100/Comp. | 5/10 | — |
| 17 | 24 | 1340 | 0.43 | 160 | 660 | 1/60 | 40/Comp. | 5/10 | — |
| 18 | 120 | 1340 | 0.61 | 200 | 710 | 1/60 | 100/Comp. | 10/20 | — |
| 19 | 24 | 790 | 0.36 | 100 | 110 | 1/60 | 100/Comp. | 30/65 | — |
| 20 | 216 | 790 | 0.86 | 220 | 570 | 1/60 | 150/Comp. | 30/50 | — |
| 22 | 24 | 1320 | 0.38 | 100 | 160 | 1/60 | 90/Comp. | 5/10 | — |
| 23 | 72 | 1320 | 0.79 | 400 | 930 | 1/60 | 130/Consid. | 5/15 | — |
| 24 | 24 | 1320 | 0.30 | 200 | 70 | 1/60 | 100/Comp. | 5/10 | — |
| 25 | 168 | 1320 | 0.70 | 720 | 830 | 1/60 | 200/Consid. | 10/15 | — |
| 28 | 1 | 1320 | 0.42 | 140 | 795 | 1/60 | Consid./Dissol. | 10/10 | — |
| 29 | 24 | 1320 | 0.78 | 500 | 820 | 1/60 | Dissol. | 10/20 | — |
| 30 | 1 | 1320 | 0.45 | 220 | 560 | 1/60 | Dissol. | 10/10 | — |
| 31 | 24 | 1320 | 0.80 | 640 | 880 | 1/60 | Dissol. | 10/10 | — | flushability by flushing them through a testing system designed for such purposes. The testing system comprises an American Standard toilet fitted with a 3 inch (I.D.) copper pipe, approximately 11–12 feet long. This pipe is connected to a toilet by way of an elbow and a suitable length of vertical placed piping. At the opposite end of the pipe, and at right angles thereto, is placed an exit pipe about 20 inches long. A tubular wire mesh screen, about 18 inches long, is concentrically placed within the exit pipe, the screen carrying several rows of barbs to simulate any internal rough surfaces in a sewage system. The test is conducted by dropping the sanitary napkin into the toilet bowl, waiting 15 seconds, and then flushing. After each napkin is flushed, the screen is removed and the residue thereon is visually rated by comparison with a set of standard photographs. A flushability rating of excellent, good, fair or poor is then assigned to the napkin under test. For comparison purposes, napkins were also prepared with the standard cover now being used in the commercially available flushable STAYFREE maxi pads. The results of these tests are reported in Table V.

TABLE V

| Sample Binder | % Solids in Solution | Solution Viscosity (Centip.) | % Add On | Flushability |
|---|---|---|---|---|
| 27 | 8% | 1200 | 15% | Fair-Excellent |
| 18 | 6% | 1200 | 15% | Fair-Excellent |
| 20 | 6% | 1200 | 15% | Good-Excellent |
| Commercial Napkin | — | — | — | Fair-Poor |

EXAMPLE 6

Samples of the napkin having a nonwoven cover employing the binder denoted as sample 26 and described in the foregoing examples, are submitted to a panel of users and are rated for their ability to withstand abrasion after use. For comparison purposes, the commercial napkin of Example 5 is likewise submitted and rated. The results are recorded in Table VI below.

TABLE VI

|  | Napkin | |
|---|---|---|
|  | Sample 26 Binder | Commercial Napkin |
| Average Time Worn (Hrs.) | 5.2 | 4.4 |
| Average Amt. of Fluid Deposited (cc) | 4.4 | 4.8 |
| ABRASION RATING (Nos. of Napkins So Rated) |  |  |
| None | 18 | 9 |
| Slight | 3 | 4 |
| Moderate | 1 | 3 |
| Very Bad - Cover Torn | 3 | 7 |
| Total No. of Napkins | 25 | 23 |

EXAMPLE 7

An ionic polyurethane binder solution (binder 18 from Table I, about 8.3 weight % solids) is used to prepare a nonwoven rayon fiber cover for a sanitary napkin. The cover is made with 1⅛-inch staple length rayon fibers in the manner described above and contains about 15 weight percent of the binder, based on the weight of the rayon fibers.

Square cover segments (15mm × 15mm) are then prepared and placed in 20-milliliter aliquots of distilled water and of aqueous 1 wt-% NaCl solution. The integrity of the segments vs. time is observed, and the observations are set forth in Table VII below.

TABLE VII

|  | Solvent Medium | |
|---|---|---|
| Time | Distilled Water | 1.0% Sodium Chloride Solution |
| 1 Minute | Complete Breakup in Fibers | Cover intact |
| 24 Hours | " | Cover intact |

A prepared napkin was then placed in 2,500 ml of each of the following media: distilled water, 1% sodium chloride solution and tap water. The materials were placed on a reciprocal shaker and subjected to oscillations which were varied between 60 and 70 per minute. The integrity of the napkins was observed. The napkins in the 1 wt-% saline solution maintained their integrity for the longest period of time. The data are presented in Table VIII, which follows.

TABLE VIII

|  |  | Breakup of Napkins in Solvent Medium | | |
|---|---|---|---|---|
| Time (mins) | Oscillations/min. | Distilled Water | Tap Water | 1% Sodium Chloride Solution |
| 1 | 60 | Parts of Cover & Pad Separated | Some Fraying of Cover | Some Fraying of Cover |
| 20 | 70 | Napkin into Slurry Form | Parts of Cover & Pad Separated | Some Fraying of Cover |

The foregoing data further demonstrates the water dispersible nature of the products of this invention.

It will be appreciated by one skilled in the art that the present cationic polyurethane binders can be designed to particularly function in a specific capacity. For example, when used in sanitary napkins, it is clear that the binders contact only absorbent materials in a localized region with menstrual fluid, whereas, when the napkins are disposed of, the napkins are fully immersed in swirling tap water. Accordingly, for binders used for those purposes, a relatively wider range of polymer ionic charge densities may be employed. On the other hand, where the binders are used in the absorbent layer for a diaper, the binders are in more substantial contact with the excreted body fluid and may have to remain in such contact for a longer time period. Accordingly, binders having relatively lower polymer ionic charge densities should be used.

What is claimed is:

1. In a nonwoven fabric which comprises a web of substantially uniformly laid fibers and a polyurethane-based binder for said fibers distributed in said web, the improvement which comprises employing as said binder a cationic polyurethane having a repeating unit of the formula:

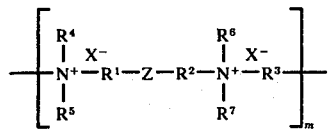

wherein $R^1$ and $R^2$ are selected from the group consisting of —$CH_2$— and alkylene containing 2 to 4 carbon atoms, inclusive; Z is a linking condensation residue of a polyisocyanate with a polyol and contains at least four urethane linkages; $R^3$ is alkylene containing 2 to 4 carbon atoms, inclusive; $R^4$, $R^5$, $R^6$ and $R^7$ are lower alkyl containing 1 to 4 carbon atoms, inclusive; X is a halogen selected from the group consisting of chlorine and bromine, and m is an integer of sufficient magnitude to provide a polymer having a molecular weight sufficient to form a solid material; the equivalent weight of the polymer, expressed as the ratio of the molecular weight of the repeating unit divided by the number of $N^+$ in the repeating unit, being from about 500 to about 2000, whereby the nonwoven fabric is resistant to body fluids but dispersible in water.

2. The nonwoven fabric in accordance with claim 1 wherein the equivalent weight of the polymer is about 750 to about 1400.

3. The nonwoven fabric in accordance with claim 1 wherein the binder is present in the web in an amount of about 4 to about 35 percent by weight, based on the weight of the web.

4. The nonwoven fabric in accordance with claim 1 wherein the binder is present in the web in an amount of about 5 to about 20 percent by weight, based on the weight of the the web.

5. The nonwoven fabric in accordance with claim 1 wherein the molecular weight of said cationic polyurethane is in the range of about 8000 to about 50,000.

6. The nonwoven fabric in accordance with claim 1 wherein $R^1$ and $R^2$ are both ethylene, $R^3$ is butenylene, $R^4$, $R^5$, $R^6$, and $R^7$ are methyl and X is chlorine.

7. The nonwoven fabric in accordance with claim 1 wherein Z contains, in addition to said urethane linkages, also ester linkages and ether linkages.

8. The nonwoven fabric in accordance with claim 1 wherein Z contains, in addition to said urethane linkages, also ester linkages.

9. The nonwoven fabric in accordance with claim 1 wherein Z contains, in addition to said urethane linkages, also ether linkages.

10. The nonwoven fabric in accordance with claim 1 wherein said cationic polyurethane includes a condensation product of a polyisocyanate and an aliphatic polyester polyol.

11. The nonwoven fabric in accordance with claim 1 wherein said binder is distributed in said web in a predetermined pattern.

12. The nonwoven fabric in accordance with claim 1 wherein said fibers are viscose rayon fibers having a length of not more than about 2 inches.

13. In an absorbent product for retaining body fluids comprising an absorbent core and a fluidpervious nonwoven fabric covering at least a portion of said absorbent core wherein said nonwoven fabric comprises a web of substantially uniformly laid fibers not exceeding about two inches in length, the improvement which comprises having a cationic polyurethane binder distributed in said web in an amount of about 5 to about 35 percent by weight of the web; said cationic polyurethane binder being selected as having a repeating unit of the formula:

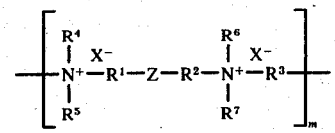

wherein $R^1$ and $R^2$ are selected from the group consisting of —$CH_2$— and alkylene containing 2 to 4 carbon atoms, inclusive; Z is a linking condensation residue of a polyisocyanate with a polyol and contains at least four urethane linkages; $R^3$ is alkylene containing 2 to 4 carbon atoms, inclusive; $R^4$, $R^5$, $R^6$ and $R^7$ are lower alkyl containing 1 to 4 carbon atoms, inclusive; X is a halogen selected from the group consisting of chlorine and bromine, and m is an integer of sufficient magnitude to provide a polymer having a molecular weight sufficient to form a solid material; the equivalent weight of the polymer, expressed as the ratio of the molecular weight of the repeating unit divided by the number of $N^+$ in the repeating unit, being from about 500 to about 2000, whereby the nonwoven fabric is resistant to body fluids but dispersible in water.

14. An absorbent product according to claim 13, wherein said absorbent core includes a fluid-pervious element.

15. An absorbent product according to claim 14, wherein the fluid-pervious element is fibrous tissue.

16. An absorbent product according to claim 14, wherein the fluid-pervious element is gauze.

17. An absorbent product according to claim 14, wherein the fluid-pervious element is plastic netting.

18. An absorbent product according to claim 13, wherein said absorbent core includes a fluid-impervious element.

19. An absorbent product according to claim 18, wherein the fluid-impervious element is polyethylene film.

20. An absorbent product according to claim 13, wherein the absorbent core includes a fluid-pervious element and a fluid-impervious element.

21. An absorbent product according to claim 20, wherein the fluid-pervious element is fibrous tissue and the fluid-impervious material is polyethylene film.

* * * * *